Nov. 20, 1956 P. B. BEGONIA Plant Pat. 1,528
ROSE PLANT
Filed Dec. 5, 1955
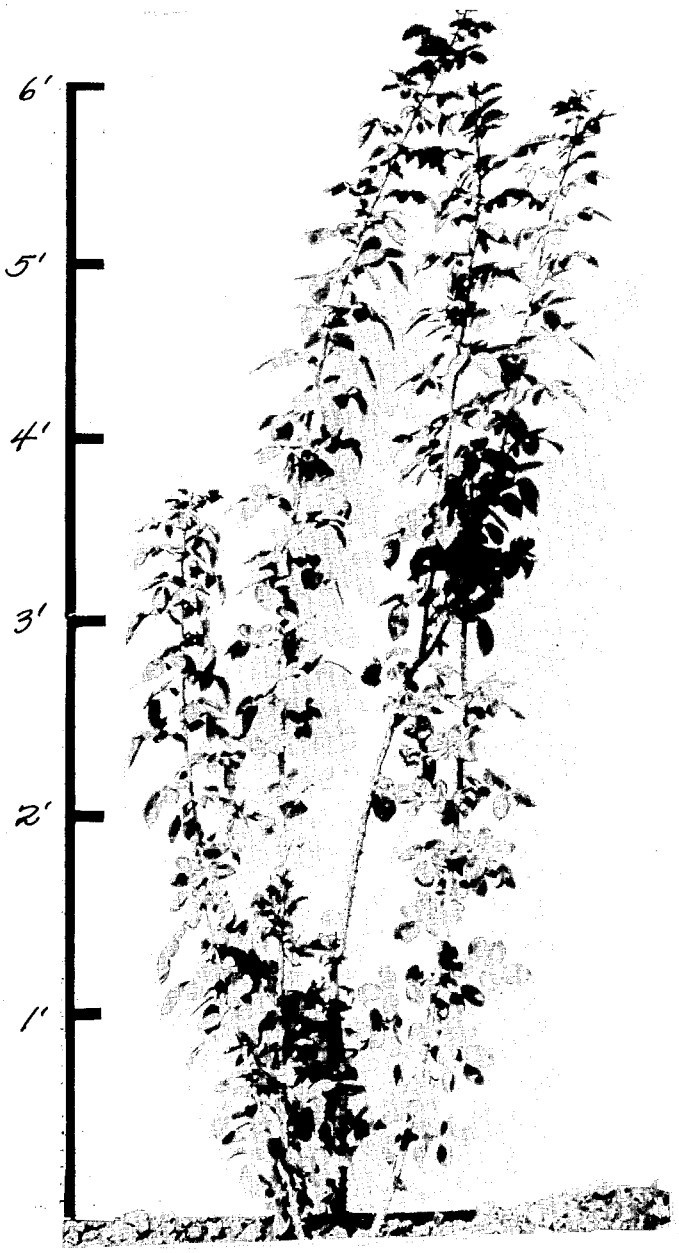
INVENTOR.
P. B. Begonia
BY
Robb & Robb
Attorneys.

United States Patent Office

Plant Pat. 1,528
Patented Nov. 20, 1956

1,528

ROSE PLANT

Paul B. Begonia, San Jose, Calif., assignor to Germain's, Inc., Los Angeles, Calif., a corporation of California Application December 5, 1955, Serial No. 551,187

1 Claim. (Cl. 47—61)

The present invention relates to a new and distinct variety of rose plant of the climber class, which was discovered by me as a bud sport of the variety "Chrysler Imperial" (Plant Patent No. 1167), but which is distinguished from the latter parent variety by its climbing habit of growth. The new variety was discovered by me amongst a cultivated block of 2-year-old "Chrysler Imperial" plants which were being grown under my direction or supervision at Livermore, California.

At the time of my discovery, my attention was attracted to the new variety by the unusually vigorous and climbing habit of a particular plant of the variety "Chrysler Imperial" in the block of plants mentioned above. Upon closer examination thereof, I found the parent plant had sported, and I thereupon promptly took steps to preserve, asexually reproduce and observe the sport for the purpose of determining whether its climbing habit was fixed and transmissible by asexual reproduction. The climbing habit was fully confirmed by such observations and by asexual reproduction by budding, as performed by me at Livermore, California, and I have established that the climbing habit of growth of the new variety comes true to form and is transmissible through succeeding propagations.

The parent variety "Chrysler Imperial" is a bush rose of the hybrid tea class, and is primarily notable for its compact habit of growth, abundance of foliage, resistance to mildew and blackspot, the distinctive form of its buds, its predominant tendency to bear its flowers singly on sturdy, medium-long stems, the reduced tendency of its buds to "ball" as they open during cool, foggy weather, and the predominant Chrysanthemum Crimson general color effect of its open flowers which appear to the eye to be of a lighter and iridescent glowing red color and with a tendency to shadings of Rose Red. However, this bush variety, so far as I am aware, has never exhibited a climbing habit, and its growth has usually been of the average strong bush rose.

The new variety herein is substantially identical to its parent in all respects, except that it is definitely a climber, as evidenced by its vigorous and strong canes which attain a height at maturity in excess of fifteen feet.

In view of the general similarities between my new variety and its parent, except as noted above, it is unnecessary to describe or illustrate the new variety in detail, since it otherwise substantially conforms to the detailed description and illustration embodied in Plant Patent No. 1167, dated February 10, 1953, to which reference may be readily had, but for convenience, the accompanying drawing illustrates in black-and-white a typical specimen plant of my new variety in association with a marked scale graduated in feet to denote the relative height of the plant, and in the following portion of this application, there is given a brief description of the new variety, with color terminology in accordance with the Horticultural Color Chart of the British Color Council, except where general color terms of ordinarv dictionary significance are obvious:

Type: Hardy; climber; for cut flowers and for garden decoration.

Class: Climbing hybrid tea.
Parentage: Sport of "Chrysler Imperial."
Propagation: Holds its distinguishing characteristics through succeeding propagations by budding.

*Flower*

Locality where grown and observed: Van Nuys, California.
Flowers borne: Usually singly, but rarely 2 or 3 to stem; on strong stems of medium length.
Quantity of bloom: Free; abundant, outdoors.
Fragrance: Centifolia.
Bud:

*Peduncle.*—Medium length; from 2¼ inches to 3¾ inches; erect; stiff; almost entirely smooth; with few prickles and small thorns near base of peduncle on very vigorous stems only. Color—medium green and heavily tinged with anthocyanin toward base.

*Before calyx breaks.*—Size—medium large. Form—ovoid; without foliaceous appendages on the surface of the bud, but with 3 of 5 sepals or every other sepal having small lateral lance-shaped appendages; with slender, much-cut foliaceous parts extending beyond the tip of the bud equal to ¼ of its length on one sepal only. Color—Oxblood Red, Plate 00823, varying to Maroon, Plate 1030.

*As calyx breaks.*—Color—Chrysanthemum Crimson, Plate 824/1.

*As first petal opens.*—Size—large. Form—long ovoid, varying to urn-shaped at times in hot weather. Color: outside—from Chrysanthemum Crimson, Plate 824/2 to Chrysanthemum Crimson, Plate 824/3; inside—near Chrysanthemum Crimson, Plate 824.

*Opening.*—Is retarded from opening by cold weather, but opens quite well even during cool, foggy weather, and opens very well in hot weather.

Bloom:

*Size (when fully open).*—Large; from 4 inches to 5 inches.

*Petalage.*—Very double; from 33 to 48 petals; arranged regularly.

*Form.*—Very high-centered at first, but becoming cupped; petals being at first tightly rolled inward, but becoming very loosely rolled outward later at maturity, and inner or central petals on older flowers raising up and covering the stamens and petals.

Petals:

*Texture.*—Thick; soft; with inside satiny-velvety and outside dull.

*Shape.*—Outside—obovate; scalloped; with apex having 1 notch. Size: width—from 2 inches to 2⅜ inches; length—from 2 inches to 2⅛ inches, with ⅓ of petals having ⅛ inch tip, but about ⅔ of petals with irregular indentation at apex instead of apical tip. Intermediate—lanceolate; color—rather uniform color throughout.

This description of a newly opened flower was made from a rose grown outdoors in the month of May, at Van Nuys, California.

*Color.*—Outer petal: outside surface—from chrysanthemum Crimson, Plate 824/2 to Chrysanthemum Crimson, Plate 824/3; inside surface—near Chrysanthemum Crimson, Plate 824. Intermediate petal: outside surface—Spiraea Red, Plate 025; inside surface—Rose Red, Plate 724. Inner petal: outside surface—Spiraea Red, Plate 025; inside surface—Rose Red, Plate 724.

This description was made from a rose that was open for 3 days outdoors in the month of May, at Van Nuys, California:

*Color.*—Outer petal: outside surface—Tyrian Purple, Plate 727/3; inside surface—Tyrian Purple, Plate 727/2, tinged with Rose Red, Plate 724 toward base. Inner petal: outside surface—Tyrian Purple, Plate 727/3; inside surface—Tyrian Purple, Plate 727/2, tinged with Rose Red, Plate 724 toward base.

*General color effect.*—Newly opened flower—from Rose Red, Plate 724 to Chrysanthemum Crimson, Plate 824/2. 3-days open—from Tyrian Purple, Plate 727/3 to Rose Red, Plate 724.

*Behavior.*—Drops off cleanly, fading to Rose Red, Plate 724; very little affected by weather, excepting that hot weather accelerates fading reaction to Rose Red, Plate 724.

*Flower longevity.*—On bush in garden—4 days in May. Cut flowers grown outdoors and kept at living-room temperatures—6 days in May.

*Reproductive organs*

Stamens: From medium number to many; arranged irregularly about pistils.

Filaments: Medium length; most with anthers. Color—Nasturtium Red, Plate 14/1.

Anthers: Small; open at various time. Color—Sulphur Yellow, Plate 1/2.

Pollen: Moderate. Color—gold.

Pistils: Many; irregularly arranged.

Styles: Uneven; short; thin; irregularly bunched. Color—light red toward upper 1/16 portion.

Stigma: Color—from pale yellow to cream.

Ovaries: All enclosed in calyx.

Hips: Globular; with inconspicuous neck, smooth; walls thick and fleshy. Color—Persimmon Orange, Plate 710/2, shading to Jasper Red, Plate 018.

Sepals: Falling soon; moderate length; curled; recurved. Color—olive green.

Seeds: None observed.

*Plant*

Foliage:

*Leaves.*—Compound of 5 to 7 leaflets; medium size; from leathery to semi-glossy.

*Leaflets.*—Shape—oval, with apex acute. Base—round. Margin—simply serrate.

*Color.*—Mature: upper surface—Spinach Green, Plate 0960/1; under surface—Willow Green, Plate 000862/1, with veins conspicuously Anthocyanin Red. Young: upper surface—Sage Green, Plate 000861; under surface—Scheeles Green, Plate 860/3, washed with Garnet Brown, Plate 00918/3.

*Rachis (the supporting stem of the compound leaf).*—Medium weight. Upper side—grooved; prickly. Under side—sparsely prickly.

*Stipules.*—Short; narrow; with points turning out at an angle of more than 45°.

*Disease resistance.*—Resistant to mildew and blackspot, as determined by observation and comparison with other varieties, particularly "Mirandy" (Plant Patent No. 632), as grown under comparable cultural conditions at Van Nuys, California.

Growth:

*Habit.*—Climber.

*Growth.*—Vigorous.

*Canes.*—Heavy.

*Main stems.*—Color—Fern Green, Plate 0862, heavily tinged with Anthocyanin Red. Thorns—many; medium length; hooked downward; with narrow base; color—Garnet Brown, Plate 00918/3. Prickles—many; color—reddish brown. Hairs—none.

*Branches.*—Color—Fern Green, Plate 0862, shading to Oxblood Red, Plate 00823/3. Prickles—many; color—reddish brown. Hairs—none.

*New shoots.*—Color—Fern Green, Plate 0862/2, shading to Rhodonite Red, Plate 0022. Thorns—many; short; hooked downward; with short, narrow base; color—Oxblood Red, Plate 00823/2. Prickles—many; color—reddish. Hairs—none.

I claim:

A new and distinct variety of rose plant of the climbing hybrid tea class, substantially as herein shown and described, characterized particularly as to novelty by being substantially identical with its parent variety "Chrysler Imperial" (Plant Patent No. 1167), but essentially being distinguished therefrom by its vigorous and climbing habit of growth.

No references cited.